United States Patent [19]

Cram

[11] 4,230,947
[45] Oct. 28, 1980

[54] APPARATUS FOR TREATING FLOWABLE MATERIAL

[75] Inventor: Robert D. Cram, Ipswich, Mass.

[73] Assignee: High Voltage Engineering Corporation, Burlington, Mass.

[21] Appl. No.: 54,002

[22] Filed: Jul. 2, 1979

[51] Int. Cl.³ ............................................. G01N 23/00
[52] U.S. Cl. ................................. 250/434; 250/432 R; 250/492 B
[58] Field of Search ........... 250/434, 438, 435, 432 R, 250/492 B, 492 R

[56] References Cited

U.S. PATENT DOCUMENTS

| 2,001,555 | 5/1935 | Trebler | 250/434 |
| 3,974,391 | 8/1976 | Offermann | 250/492 B |
| 4,048,504 | 9/1977 | Bosshard | 250/434 |
| 4,173,719 | 11/1979 | Tauber et al. | 250/434 |

Primary Examiner—Bruce C. Anderson

Attorney, Agent, or Firm—Russell & Nields

[57] ABSTRACT

An apparatus for treating flowable material falling through an irradiation zone in the form of a thin, substantially nonturbulent, cohesive layer including in combination an outlet reservoir adapted to catch the falling material after it is irradiated; a source of radiation adapted to direct radiation against the layer as it falls through the irradiation zone; and means for forming flowable material flowing through a pipe or similar material transfer means into a thin, substantially nonturbulent, cohesive layer and directing the layer so formed through the irradiation zone, said means having an inlet orifice adapted to receive material from the transfer means and convey it to an upwardly extending transition zone wherein the flow is gradually widened prior to its entry into a gradually upwardly sloped approach zone which terminates at a forward edge over which the material passes in the appropriate form for treatment in the irradiation zone.

9 Claims, 7 Drawing Figures

APPARATUS FOR TREATING FLOWABLE MATERIAL

BACKGROUND

1. Field of the Invention

This invention relates generally to an apparatus for treating flowable material by the irradiation thereof with electrons or other radiation, and more particularly to a device of this type wherein the material is presented to a radiation beam in the form of a substantially uniform, and cohesive thin layer.

2. Summary of Prior Art

Numerous proposals for treating flowable materials with radiation are known, particularly in the area of treating drinking water, sewage, and the like with electrons for the removal of pathogenic microorganisms and other beneficial results. In each of these proposals, the importance of presenting the material to the radiation beam as a thin layer of substantially uniform thickness so as to allow the radiation impinging on such a layer to penetrate therethrough and thereby treat all the material also has been recognized. It has further been recognized that excessive turbulence in the flow of material is to be avoided and that the tendency of flowable materials to form rivulets which increase in thickness the further the material travels over a metal surface should be controlled in order that a substantially uniform level of treatment may be assured for all material presented to the radiation beam. To accomplish this prior proposals have suggested the use of Bernoulli throats as shown in U.S. Pat. No. 3,901,907; open slanted trays as shown in U.S. Pat. No. 3,591,491, or funnels as shown in U.S. Pat. No. 4,074,138; and the use of a trough having a slot in the bottom thereof either with or without a system of counter-rotating rollers for accelerating the flow as shown in U.S. Pat. No. 4,048,504.

Each of these proposals has drawbacks, however. The Bernoulli throat configuration is expensive to build and install and requires added radiation energy to assure penetration through the throat wall and the material; the slanted tray has a limited throughput capability and a somewhat turbulent flow causing nonuniformities in treatment; the rotating drum also has a limited throughput since the radial acceleration of the material must not be so great as to hurl the material off the drum, not to mention sludge build up problems and rather high capital installation and maintenance costs; and the slotted trough also has a tendency toward sludge build up and toward irregularities and discontinuities in flow when counter-rotating rollers are used.

SUMMARY OF THE PRESENT INVENTION

Accordingly, it is an object of the present invention to provide a device for treating flowable materials with radiation which is comparatively simple and inexpensive to install and maintain and which is capable of handling large throughput levels.

It is also an object of the present invention to provide a device of the above type wherein sludge buildup is not a problem, yet the flow is uniform, cohesive, and not excessively turbulent.

In general the invention provides an apparatus for treating flowable material with radiation in which the material inputed into the device is formed into a thin, substantially nonturbulent, cohesive layer which is directed over a forward edge so as to fall under the influence of gravity through an irradiation zone. More particularly this apparatus includes first means forming an irradiation zone, second means forming an outlet reservoir, and third means for forming inputed material into a thin, substantially nonturbulent cohesive layer and directing the layer so formed through the irradiation zone. The third means includes an inlet orifice adapted for connection to a source of material to be treated which orifice opens into an upwardly extending transition zone which in turn opens into an upwardly sloping approach zone which terminates at a forward edge disposed above the irradiation zone, the second means being disposed opposite the forward edge below the irradiation zone. It is contemplated that the flow of material passing through the device will be gradually widened in the transition zone thereby tranquilizing the flow so that it enters the approach zone as a comparatively thick, but tranquil, layer. The gradual upward slope of the approach zone, contemplated to be between 1:10 and 1:30, creates a transitional flow condition which results in a uniform and cohesive sheet of material after the material has passed over the forward edge. The forward edge preferably has a radius between zero and substantially about ½ inch to control the incidence and amount turbulence and the horizontal motion components imparted to the layer of material flowing thereover according to the particular properties present in the material being treated and the rate of flow desired.

BRIEF DESCRIPTION OF THE DRAWINGS

These as well as other features, objects, and advantages of the present invention will become more apparent from the following detailed description of a preferred embodiment thereof and the appended claims taken in conjunction with the accompanying drawings in which:

DETAILED DESCRIPTION OF PREFERRED EMBODIMENT

Figure 1:
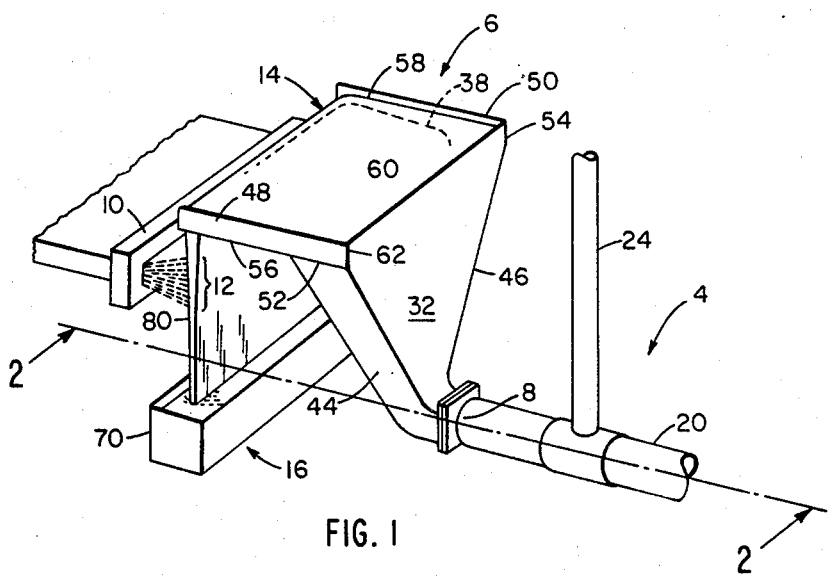
FIG. 1 is a perspective view of an apparatus in accordance with the present invention showing a typical flow of material therethrough.

Referring now specifically to the drawings, wherein like reference numerals are used to designate like elements throughout, and in particular to FIG. 1, there is therein shown a perspective view of an apparatus for treating flowable material with radiation in accordance with the present invention. Generally, this apparatus includes inlet means generally indicated at 4 for conveying material from a source, for example a sewage treatment facility, not shown, connected to material spreading means, generally indicated at 6, via an orifice 8 therein; irradiation means 10 defining an irradiation zone 12 below the output 14 of spreading means 6; and an outlet reservoir 16 below irradiation zone 12 adapted to catch material falling from output 14 through irradiation zone 12. The details of the construction of this apparatus and the mechanics of material flow therethrough will be best understood with reference to FIG. 2 which is a cross-sectional view of the apparatus of FIG. 1 taken along the line 2—2.

Figure 2:
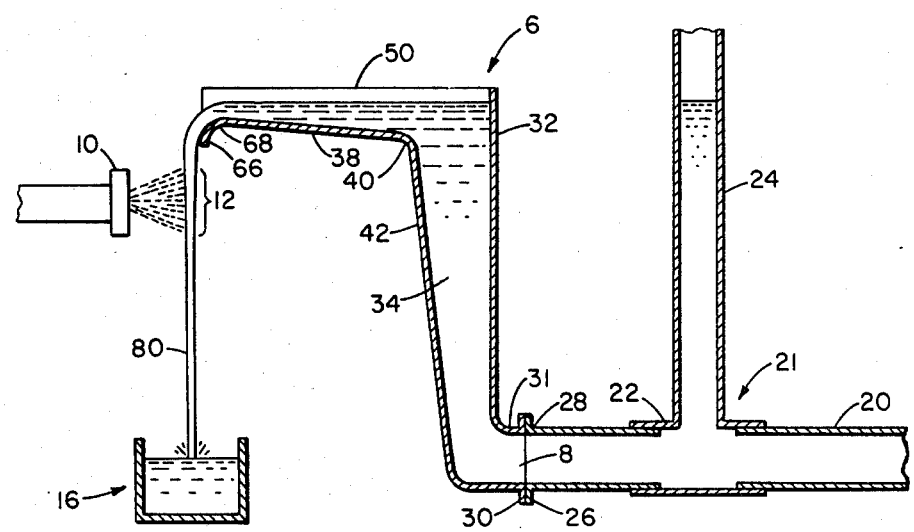
FIG. 2 is a cross-sectional view of the apparatus shown in FIG. 1 taken along the line 2—2.

As will be seen from FIG. 2, the inlet means 4 of this embodiment which connects the rest of the apparatus to the material source is a pipe 20. I have found that pipe 20 should be at least ten to twelve times its diameter in length, be straight, and contain debubbling means 21 for removing air pockets introduced into the flow by leaking pump packings and the like in order to avoid the creation of undesirable flow disturbances in the remainder of the apparatus. The debubbling means 21 may be any means known to the art for this purpose, however, I have found that a simple tee joint 22 disposed in pipe 20 between the source (not shown) and the orifice 8 having a vent 24 extending vertically upward therefrom works reasonably well for this purpose. The pipe 20 is connected to material spreading means 6 so as to allow material flowing through pipe 20 to enter the spreading means 6 through orifice 8. This connection may be accomplished in any convenient manner, but will generally include the joining of a flange 26 attached to the periphery of end 28 of pipe 20 to a flange 30 attached to the periphery of orifice 8 by welding or bolting same together.

Material spreading means 6 in this embodiment includes a short conduit 31 connecting orifice 8 to the narrow lower portion of side 32 of upwardly extending wedge-shaped cavity 34. A gradually upwardly slopping ramp 38 extends outwardly of the top 40 of side 42 of cavity 34, side 42 being shorter than side 32. Sides 44 and 46 of cavity 34 rise to the same height as side 42. Wall portions 48 and 50 rise upwardly from the tops 52 and 54 of sides 44 and 46 and from edges 56 and 58 of ramp 38 to a height level with the top 60 of side 32, ends 62 and 64 of wall portions 48 and 50 being connected to those portions of side 32 adjacent thereto. A downwardly curved forward edge 66, having a radius of curvature of between zero and substantially about ½ inch, is located at the extreme outer edge 68 of ramp 38.

At least one radiation beam generator 10 is located beneath the level of the forward edge 66 so as to define an irradiation zone in the area beneath the edge 66 and above the outlet reservoir 16, which is generally contemplated to be a rectangular trough 70 disposed below the edge 66 so as to catch material falling thereover. This trough 70 may be used to store the treated material, but more generally will include means (not shown) for allowing the treated material to flow therefrom to other apparatus for further treatment or to a permanent storage facility.

It will thus be seen that the material to be treated flows from inlet pipe 20 through orifice 8 and conduit 30 into the narrow end of wedged-shaped cavity 34 as a substantially continuous, uniform stream with few if any air pockets trapped therein under the influence of an external pump (not shown) the hydraulic pressure of which maintains the level of material in the spreader at the desired level. As the material is forced upward in cavity 34 it is tranquilized by the affect of the gradually expanding area into which it flows until it reaches the top 40 of side 42. At this point the flow proceeds up ramp 38 whose slope is generally contemplated to be between 1:10 and 1:30 in order to create a transitional flow condition which results in a uniform and cohesive layer falling through irradiation zone 12. It will be understood that by so doing the flow of material is changed from its original circular cross section to a comparatively thick layer and finally to a thin layer as it passes over the edge 66. The curvature of the edge 66 is important in the maintenance of the cohesiveness of the layer falling therefrom through the irradiation zone and in controlling the disposition of the falling layer in that zone. Thus, if the curvature of the edge is too large the falling layer will not be cohesive, yet if it is too small an undesirable horizontal component of motion may be imparted to the layer which component may adversely effect the spacial orientation of the falling layer relative to the radiation source. Obviously, the flow rate and the properties of the particular material being treated have some effect upon the optimum radius of curvature appropriate for the edge, however, I have found that a radius of curvature of between zero and about ½ inch works well for flow rates as high as 120 gallons/minute over a 50 inch forward edge for materials having less than 10% solids content.

The beam generator 10 disposed laterally on either or both sides of the thin flat layer 80 falling from the edge 66 is contemplated to be of a standard type suitable for directing radiation substantially perpendicularly against the falling layer 80. Generally, this will mean that a beam which fans out vertically as it proceeds from the generator 70 to the layer 80 will be played back and forth across the horizontal width of the layer 80 at a speed many times greater than the speed at which the material making up the layer falls so that all material falling through the substantially rectangular irradiation zone will in theory, be uniformly treated. In fact, however, uniform treatment while substantially obtained by the above is not perfect.

The thickness and velocity of the layer varies as the layer 80 falls from the edge 66 to the outlet reservoir 16 generally as is shown in FIG. 2. Accordingly, if the disposition of the radiation beam generator 70 is fixed relative to edge 66 the beam strength will necessarily vary according to the solids content of the material in order to assure complete material treatment. Alternatively, means (not shown) may be provided for adjusting the distance of a between edge 66 and irradiation zone 12. Such adjustability permits irradiation to be accomplished at the point along the full of the material from edge 66 to reservoir 16 at which the velocity and thickness of the falling layer are most closely matched to the penetrating capability of the beam. It has also been found that the edges of falling layer 80 pull inward at a rate of about 1 inch for every 4 inches of vertical drop as surface tension forms thickened areas 90 and 91, FIG. 3, along these edges. Not only may these areas be too thick be too treated with a beam suitable for penetration of the rest of the layer, but due to the deflection of the beam, the beam is weakest in the areas adjacent to the edges of the falling layer with the result that treatment levels in these areas may not be uniform.

Figure 3:
FIG. 3 is a diagrammatic cross-sectional view taken along the line 3—3, of a typical layer of material passing through the apparatus of FIG. 1.
Figure 4:
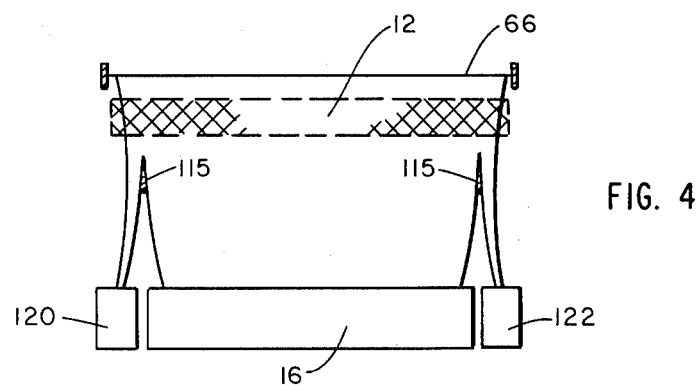
FIG. 4 is an end view of the apparatus shown in FIG. 1 including means for trimming the material flow.
Figure 5:
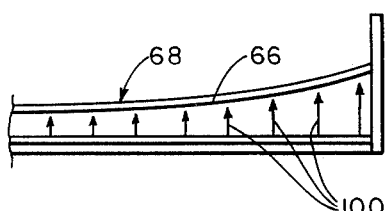
FIG. 5 is a plan view of a section of another configuration of the forward edge suitable for use in the present invention to profile the material flow.
Figure 6:
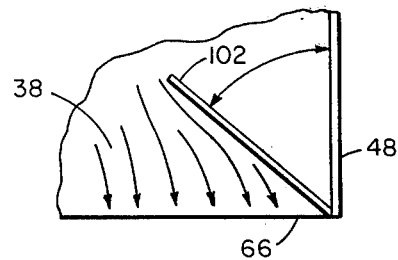
FIG. 6 is a plan view of a modified approach zone suitable for use in the present invention to profile the material flow.
Figure 7:
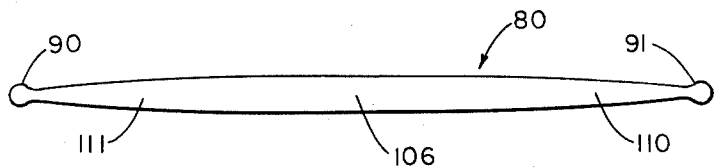
FIG. 7 is a diagrammatic cross-sectional view of a profiled material flow.

To correct for these problems, the cross-section of the layer 80, shown in FIG. 3. may be altered (hereinafter "profiled") so as to minimize the amount of material in the areas subject to treatment level nonuniformities, and the remaining material in these areas may be segregated from uniformly treated material for recycling or disposal as waste. I have found that by creating a downward bow in the edge 66 on the order of 0.06" to 0.12" from the horizontal as shown in FIG. 5 using adjustment screws indicated by arrows 100, or by the use of adjustable diverting vanes 102 normal to ramp 38 angling inwardly from the ends 104 of the edge 66 as shown in FIG. 6 the cross section of layer 80 shown in FIG. 3 may be profiled so as to correspond to that shown in FIG. 7. This cross section is tapered toward its ends and still exhibits the creation of thickened areas 90 and 91 at its edges, however, its central area 106 is substantially uniform in thickness and uniform treatment of the material in central area 106 may be assured. As has already been mentioned beam strength is weakest in treating tapered areas 110 and 111 and this combined with layer thickness variations in these areas results in a situation wherein uniform treatment of material in areas 110 and 111 cannot be assured as in some cases, such as purification of drinking water, it must be. The solution to this is simply to segregate the safe from the questionable portions of the layer before they have a chance to intermix. One way to accomplish this is shown in FIG. 4. After the layer passes over the edge 66 and through the radiation zone 12 it encounters trimming means 115 each of which may be a jet of air, a jet of water, or a knife edge disposed normal to the layer or any other means suitable to split areas 110 and 111 from area 106 in such a way that they may be collected in catching means 120 and 122 rather than outlet reservoir 16 for recycling or disposal.

It will be understood that the embodiments and practices described and protrayed herein have been presented by way of disclosure, rather than limitation, and that various substitutions, modifications and combinations may be effected without departure from the spirit and scope of this invention in its broader aspects.

I claim:

1. An apparatus for treating flowable material by the irradiation thereof comprising in combination:
    (a) a container for holding a quantity of such material including
        (1) a base portion having front, rear, left, and right edges, a rear section, and a front section, said rear section including front and rear end walls and convergent side walls defining an open substantially wedge-shaped cavity, and said front section including a flat substantially rectangular ramp extending on an upward slant from the top of said front end wall to the front edge of said base; and
        (2) vertical side walls rising from the left, right, and rear edges of said base, said side walls being appropriately connected to each other along the left-rear and right-rear corners thereby defined;
    (b) inlet conduit means connecting the interior of said container with a source of material to be irradiated through the lower portion of said rear end wall;
    (c) material delivery means associated with said inlet conduit means for delivering material to be irradiated through said inlet conduit means and into the interior of said container at a predetermined rate selected so as to cause the material filling said container to flow over the front edge of said base portion as a thin, nonturbulent, cohesive layer without overflowing said vertical side walls;
    (d) irradiation means disposed for directing at least one beam of radiation substantially perpendicularly onto the layer of material falling from the front edge of the base portion under the influence of gravity, said beam being moved back and forth across said layer at a speed much faster than that at which the material contained in said layer falls such that all material falling through the irradiation zone wherein the beam impinges upon the layer is substantially uniformly treated; and
    (e) outlet reservoir means disposed to catch the material falling from the irradiation zone.

2. The apparatus of claim 1 wherein the rate of the upward slant of the ramp is between 1:10 and 1:30.

3. The apparatus of claim 1 or claim 2 wherein the front edge of the base portion is curved downwardly to form a lip having a radius of curvature of between zero and substantially about ½".

4. The apparatus of claim 1 further including means for profiling the cross-sectional configuration of the layer.

5. The apparatus of claim 4 wherein said profiling means includes means for creating a downward bow in the front edge of the base portion.

6. The apparatus of claim 4 wherein said profiling means includes first and second vertical vanes pivoted to said left and right vertical walls respectively adjacent the front edge of the base portion for variable movement into and out of the flow of material along the ramp.

7. The apparatus of claim 1 or of claim 4 including means for segregating uniformly treated material from nonuniformly treated material said means being disposed below the irradiation zone and comprising left and right means for deflecting a portion of the left half of the layer to the left of its prior direction of fall, and deflecting a portion of the right half of the layer to the right of its prior direction of fall respectively, and left and right catching means adapted to catch the left and right deflected portions respectively and to maintain said portions separate from the remainder of said material.

8. The apparatus of claim 1 wherein the inlet means includes means for removing pockets of trapped gas in the material in the conduit prior to the introduction of the material into the container.

9. The apparatus of claim 1 or of claim 4 further including means for varying the vertical distance between the forward edge and the irradiation zone thereby providing control means governing the velocity and thickness of material being irradiated.

* * * * *